United States Patent [19]
Thompson et al.

[11] Patent Number: 6,106,789
[45] Date of Patent: *Aug. 22, 2000

[54] ALKYLATION REACTOR WITH INTERNAL ACID COOLING ZONES

[75] Inventors: Max W. Thompson, Bartlesville, Okla.; John S. Olson, Borger, Tex.

[73] Assignee: Phillips Petroleum Company, Bartlesville, Okla.

[ * ] Notice: This patent is subject to a terminal disclaimer.

[21] Appl. No.: 08/176,612

[22] Filed: Dec. 30, 1993

[51] Int. Cl.[7] ........................................ F28D 7/00
[52] U.S. Cl. .................... 422/201; 422/193; 422/230; 165/145; 165/157; 165/DIG. 429; 585/709
[58] Field of Search ...................... 422/201, 193, 422/195, 230, 231; 585/709, 714, 719, 720, 723; 165/145, 157, DIG. 429, DIG. 430, DIG. 431

[56] References Cited

U.S. PATENT DOCUMENTS

| | | | |
|---|---|---|---|
| 2,308,786 | 1/1943 | Smith | 196/10 |
| 2,386,681 | 10/1945 | Hadden | 585/720 |
| 2,887,365 | 5/1959 | Rycker et al. | 422/148 |
| 3,133,128 | 5/1964 | McDonald | 585/720 |
| 3,169,152 | 2/1965 | Van Pool et al. | 585/701 |
| 3,173,763 | 3/1965 | Miller et al. | 422/201 |
| 3,212,860 | 10/1965 | Vernon | 422/201 |
| 3,281,213 | 10/1966 | Waddill | 422/235 |
| 3,485,893 | 12/1969 | Mayhue | 585/727 |
| 3,501,536 | 3/1970 | Borst, Jr. | 585/723 |
| 3,763,264 | 10/1973 | Chapman | 585/712 |
| 3,910,771 | 10/1975 | Chapman | 422/230 |
| 3,963,072 | 6/1976 | Wagner | 165/157 |
| 3,982,903 | 9/1976 | Anderson | 422/201 |
| 4,000,212 | 12/1976 | Chapman | 585/717 |
| 4,024,200 | 5/1977 | Vora | 585/720 |
| 4,193,447 | 3/1980 | Fah | 165/145 |
| 4,225,742 | 9/1980 | Hutson, Jr. | 585/723 |
| 4,342,876 | 8/1982 | Klingman | 560/77 |
| 4,411,773 | 10/1983 | Gross | 208/164 |
| 4,538,676 | 9/1985 | Premel et al. | 165/145 |
| 4,807,698 | 2/1989 | Köhnen et al. | 165/145 |
| 5,120,895 | 6/1992 | Child et al. | 585/709 |
| 5,196,626 | 3/1993 | Child et al. | 585/720 |
| 5,196,627 | 3/1993 | Owen | 585/723 |
| 5,196,629 | 3/1993 | Owen et al. | 585/723 |
| 5,296,199 | 3/1994 | Kwok et al. | 422/201 |
| 5,333,681 | 8/1994 | Jullien et al. | 165/82 |

OTHER PUBLICATIONS

Shreves Chemical Process Industries, 1984, pp. 743 and 744.

Primary Examiner—Christopher Kim
Attorney, Agent, or Firm—Ryan N. Cross

[57] ABSTRACT

The invention provides an improved alkylation process and reactor apparatus. The invention utilizes a vessel containing a riser-reactor conduit, an acid settler and an acid cooler. Hydrocarbons are introduced beneath said riser-reactor conduit, mixed with acid catalyst, and passed generally upwards through the riser-reactor conduit to enter the acid settler. Within the acid settler, alkylate is separate from the acid catalyst and is removed from the vessel. Acid catalyst from the acid settler is cooled in the internal acid coolers and returned to the region beneath the riser-reactor conduit.

6 Claims, 6 Drawing Sheets

6,106,789

ALKYLATION REACTOR WITH INTERNAL ACID COOLING ZONES

BACKGROUND OF THE INVENTION

The invention relates to the alkylation of hydrocarbons. In one of its aspects, the invention relates to a low inventory alkylation reactor with an internal acid cooler.

Alkylation is a reaction in which an alkyl group is added to an organic molecule. Thus, an isoparaffin can be reacted with an olefin to provide an isoparaffin of higher molecular weight. Industrially, the concept depends on the reaction of $C_2$ to $C_5$ olefins with isobutane in the presence of an acidic catalyst to produce a so-called alkylate. This alkylate is a valuable blending component in the manufacture of gasolines due not only to its high octane rating but also to its sensitivity to octane enhancing additives.

Industrial alkylation processes have historically used hydrofluoric or sulfuric acid catalysts under relatively low temperature conditions. Acid strength is preferably maintained at 88 to 94 wt. % by the continuous addition of fresh acid and a continuous withdrawal of spent acid.

One of the major problems associated with the catalytic alkylation of hydrocarbons lies in handling the alkylation catalyst, that is, transporting the catalyst through the various parts of the reaction and recovery system. The problem is particularly aggravated with acid catalysts, such as hydrofluoric acid, sulfur acid, etc., since these materials share inherent drawbacks including environmental and safety concerns, acids consumption, and sludge disposal. Another problem associated with catalytic alkylation lies in dissipating the heat generated during the alkylation reaction so as to avoid overheating and polymerization of the reactants. Therefore, it is always important in alkylation processes to develop safer and more effective ways of handling the alkylation catalysts and reactants.

SUMMARY OF THE INVENTION

It is one object of this invention to provide a safer alkylation unit by reducing the acid volume requirements and yet maintaining the necessary acid concentration in the reactor.

Another object of this invention is to provide a safer alkylation process by minimizing the possibility of the acid leaking into the atmosphere.

In accordance with this invention, there is provided an apparatus, for contacting a feed with an acid catalyst to produce a product, which comprises a vertically disposed vessel having an upper end portion and a lower end portion; an acid settler contained within said vessel and located in said upper end portion; a riser-reactor conduit vertically disposed within said housing and having an inlet in fluid flow communication with said lower end portion and an outlet in fluid flow communication with said acid settler; means for introducing said feed into said housing at said lower end portion such that said feed moves upward through said riser-reactor conduit carrying with it acid catalysts contained in said lower end portion; and cooling means contained within said vessel and located beneath said acid settler and in fluid flow communication with said acid settler and said lower end portion such that said acid catalyst from said acid settler flows into said cooling means, is cooled and subsequently flows into said lower end portion.

According to another aspect of the invention there is provided an alkylation process which comprises the steps of: introducing a hydrocarbon mixture of isoparaffin and olefinic hydrocarbons into the lower end portion of a vertically disposed vessel containing a separated stream of liquid acid catalyst so that said hydrocarbon mixture and said acid catalyst commingle and travel generally upward through a vertically disposed riser-reactor conduit contained within said vessel. Within the riser-reactor conduit, isoparaffin and olefin are reacted in the presence of the acid catalyst. Subsequently, the acid catalyst and reacted hydrocarbons are passed into an acid settling zone, contained within the upper portion of the vessel, wherein the acid catalyst separates from the reacted hydrocarbons by means of said reacted hydrocarbons having a lesser density that the acid catalyst such that the less dense hydrocarbons flow generally upward and the more dense acid catalyst flows generally downward. Subsequently, the acid catalyst is passed into at least one cooling zone contained within the vessel wherein the acid catalyst continues to flow downward and is cooled by indirect heat exchange with a coolant to form a cooled acid catalyst. Finally, the cooled acid catalyst is passed into the lower portion of the vertically disposed vessel as a separated stream of liquid acid catalyst.

DETAILED DESCRIPTION OF THE INVENTION

Figure 1:
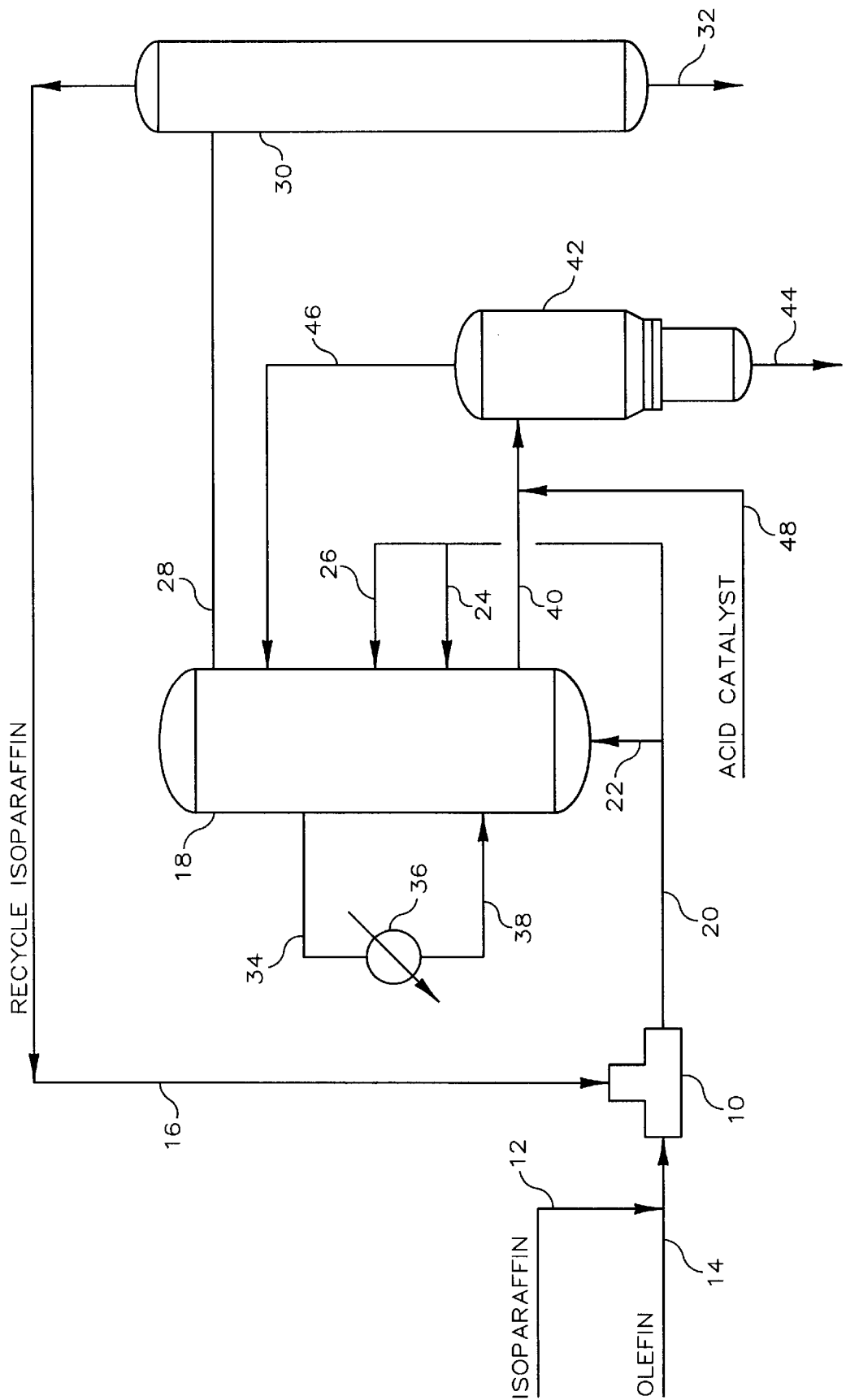
FIG. 1 is a simplified diagrammatic illustration showing an alkylation process in which an apparatus according to the invention can be used.

Referring now to FIG. 1 of the drawings, isoparaffin, olefin feed, and recycle isoparaffin enter feed-recycle mixture 10 via conduits 12, 14 and 16. The resulting hydrocarbon mixture is charged to alkylation reactor 18 via conduits 20, 22, 24 and 26. It is within the scope of the invention for the hydrocarbon mixture to be charged to the alkylation reactor 18 solely through the bottom of the reactor via conduit 22 or, optionally, for the hydrocarbon mixture feedstream to be split into two or more streams with a first stream entering the alkylation reactor 18 at the bottom via conduit 22 and other streams entering the reactor at an elevated point such as via conduits 24 and 26 as shown in FIG. 1. Within reactor 18 the hydrocarbon mixture is contacted with a liquid acid catalyst so that the isoparaffin reacts with the olefin to produce an alkylate.

A variety of alkylation catalyst can be employed as the acid catalyst in the alkylation process and reactor of the current invention, including well known catalysts, such as sulfuric acid, hydrofluoric acid (HF), phosphoric acid, metal halides, such as aluminum chloride, aluminum bromide, etc., or other alkylation catalysts; however, hydrofluoric acid is preferred.

Subsequent to the contacting of the hydrocarbon mixture and catalyst, the alkylate product and acid catalyst in alkylation reactor 18, as well as any unreacted hydrocarbons and any alkyl fluoride by-products, are passed into a settler where the less dense hydrocarbons are separated from the more dense acid catalyst by gravity such that the less dense hydrocarbons, including the alkylate product, flow toward the top of reactor 18 and the more dense acid catalyst flows toward the bottom of reactor 18. Subsequently, the alkylate is removed from the top of reactor 18 via conduit 28 and passed into fractionator 30 where unreacted isoparaffin is separated from the alkylate product. The unreacted isoparaffin is taken off the top of fractionator 30 and recycled back to alkylation reactor 18 via conduit 16, mixer 10 and conduit 20. Alkylate product is taken off the bottom of fractionator 30 via conduit 32.

The downward flowing liquid acid catalyst in alkylation reactor 18 is cooled by means of a heat exchanger internal to the reactor 18. Coolant from the reactor exits the reactor via conduit 34, circulates through a cooler 36 and re-enters the reactor via conduit 38.

Additionally, when HF catalyst is used, HF catalyst can be extracted from the reactor via conduit 40. HF catalyst in conduit 40 is introduced into acid regeneration vessel 42. The bottoms of acid rerun vessel 42 are removed through conduit 44 and are treated to produce acid soluble oil (ASO) product. The HF catalyst is removed from the top of acid regeneration vessel 42 and introduced into the settler contained in alkylation reactor 18 via conduit 46. Additionally, make-up HF catalyst can be introduced into conduit 40 via conduit 48 when needed.

Figure 2:
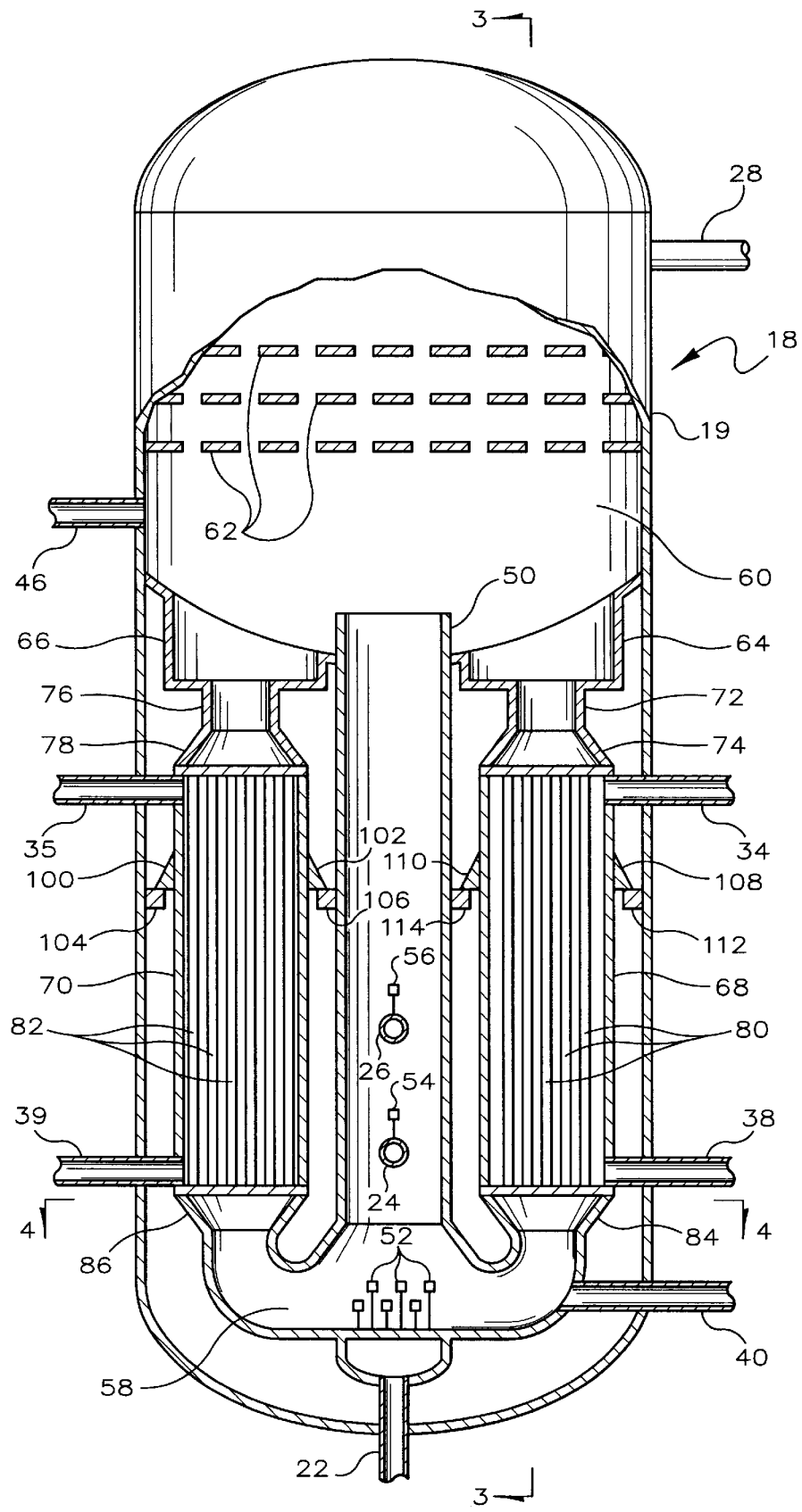
FIG. 2 is an elevation view, partially in section, showing a reactor according to the current invention.
Figure 3:
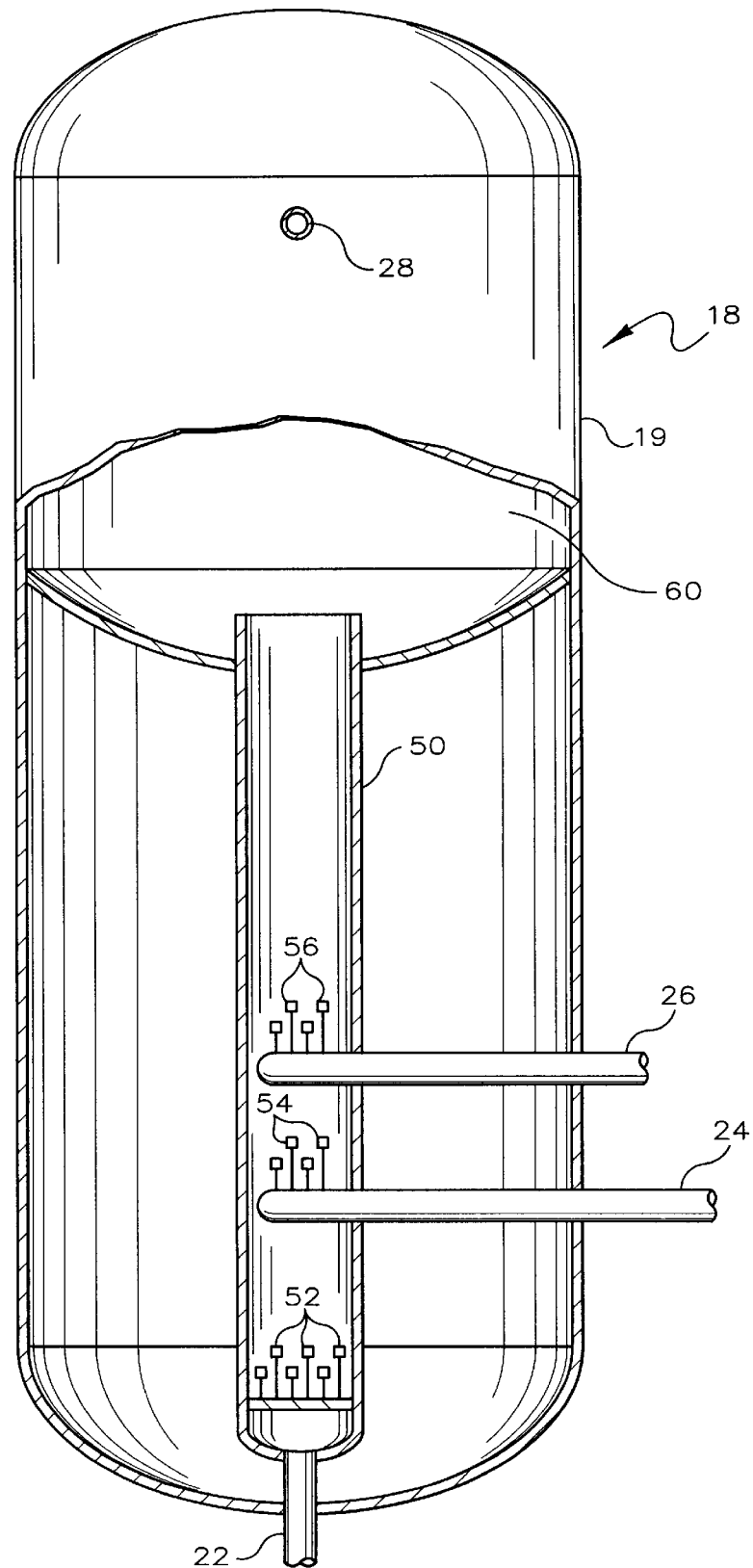
FIG. 3 is an elevation view, partially in section, taken along line 3—3 of FIG. 2.
Figure 4:
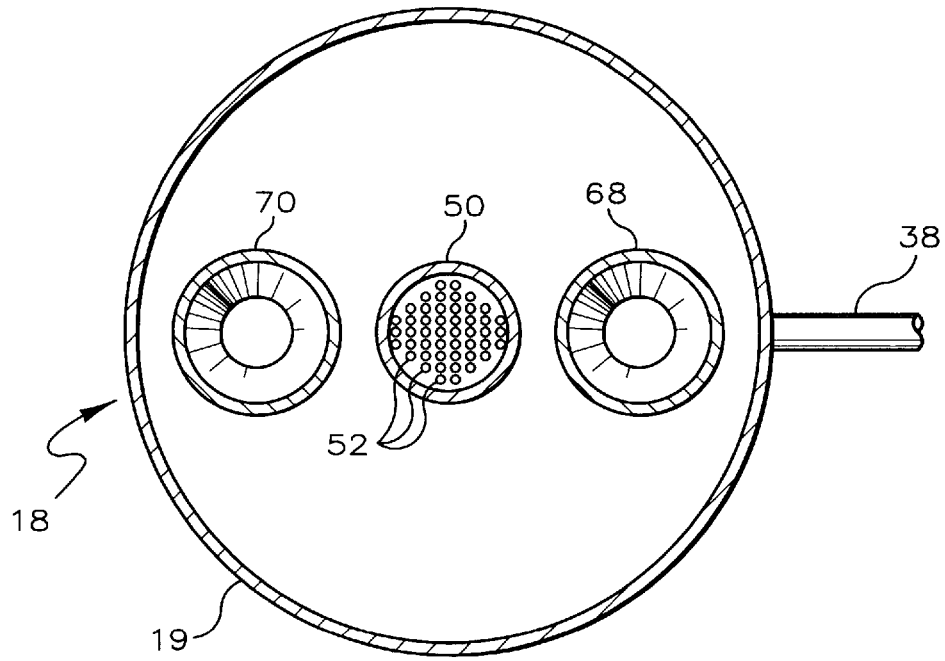
FIG. 4 is a sectional plane view through a portion of the lower end of the apparatus, taken along line 4—4 of FIG. 2 of the drawing.

Referring now to FIGS. 2, 3, and 4, an elevation view of the reactor can be seen with a cut-away view of the interior. FIG. 3 is a view of reactor 18 taken along line 3—3 of FIG. 2 with portions of the reactor cut away to better illustrate the interior. Reactor 18 comprises vertically disposed vessel 19, riser-reactor conduit 50, which is vertically disposed within vessel 19, settler 60, heat exchangers 68 and 70, and chamber 58. Vessel 19, which is preferably a double-walled vessel, has a lower end portion which contains chamber 58 and an upper end portion which contains settler 60. Riser-reactor conduit 50 and heat exchangers 68 and 70 are contained in vessel 19 and extend between the upper and lower end portions of vessel 19 and each is in fluid flow communication with both settler 60 and chamber 58.

Hydrocarbon mixture enters reactor 18 through conduits 22 and optionally, through conduits 24 and 26. Upon entering the reactor, hydrocarbon mixture from conduit 22 is released into chamber 58 below riser-reactor conduit 50; preferably, the hydrocarbon fluid is released through a spraying or injecting means such as nozzles 52. Additional hydrocarbon mixture can be introduced into the reactor and into riser-reactor conduit 50 via conduits 26 and 24. Hydrocarbon mixture entering conduits 24 and 26 are preferably introduced by a similar spraying or injecting means as used with hydrogen mixture entering through conduit 22, such as nozzles 54 and 56. Hydrocarbon mixture entering through nozzles 52 commingles with acid catalyst contained in the lower portion of alkylation reactor 18 such as that in chamber 58. The hydrocarbon, because of its lower density and due to the velocity imparted by the nozzles 52, will generally flow upwards through riser-reactor 50 carrying along with it the entrained acid catalyst from chamber 58. As the hydrocarbon mixture flows up through riser-reactor conduit 50 with the acid catalyst, the olefins and paraffins therein will react to form alkylate. Additionally, the hydrocarbon mixture introduced by nozzles 54 and 56 will add to the upward flowing effect and the isoparaffin and olefin contained therein will react to form additional alkylate.

The effluent from riser-reactor 50 containing alkylate product, unreacted olefin, isoparaffins and acid catalyst, as well as by-products will flow into settling chamber 60. Settling chamber 60 contains sieve trays 62 to provide additional contacting of acid from conduit 46 and to aid in the separation of acid catalyst from alkylate. Within settling chamber 60, hydrocarbons from the reactor effluent, which are less dense than the acid catalyst, will tend to flow toward the top of the settling chamber 60, where they are removed from alkylation reactor 60 via conduit 28. Acid catalyst from the riser-reactor effluent and additional acid catalyst introduced via conduit 46 will tend to flow down into nozzles 64 and 66 because the acid catalyst is more dense than the hydrocarbon contained within the effluent. Generally, it is preferred to maintain sufficient acid catalyst in reactor 18 so that the acid catalyst level in settler 60 stays above the top of riser-reactor conduit 50.

Acid catalyst in nozzles 64 and 66 will enter heat exchangers 68 through spool piece 72 and its associated heat exchanger endcap 74 and through spool piece 76 and its associated heat exchanger endcap 78, respectively. The acid catalyst will continue to flow down through heat exchangers 68 and 70 through tubes 80 and 82 by means of gravity. The acid catalyst flowing through heat exchangers 68 and 70 are cooled by means of coolant flowing through the shell side of the heat exchangers. Coolant enters heat exchanger 68 through conduit 38 and exits through conduit 34. Similarly, coolant enters heat exchanger 70 through conduit 39 and exits through conduit 35. The now cooled acid catalyst exits heat exchangers 68 and 70 through heat exchange endcaps 84 and 86, respectively, and enters into chamber 58. In chamber 58, acid catalyst can be removed through conduit 40 for treatment in the acid regeneration vessel.

In FIG. 4, a sectional view of the embodiment of the invention of FIGS. 2 and 2 can be seen. The sectional view is taken along line 4—4 of FIG. 2. FIG. 4 illustrates the relative positions of heat exchangers 68 and 70 in relation to riser-reactor conduit 50 for the embodiment of FIG. 2.

Figure 5:
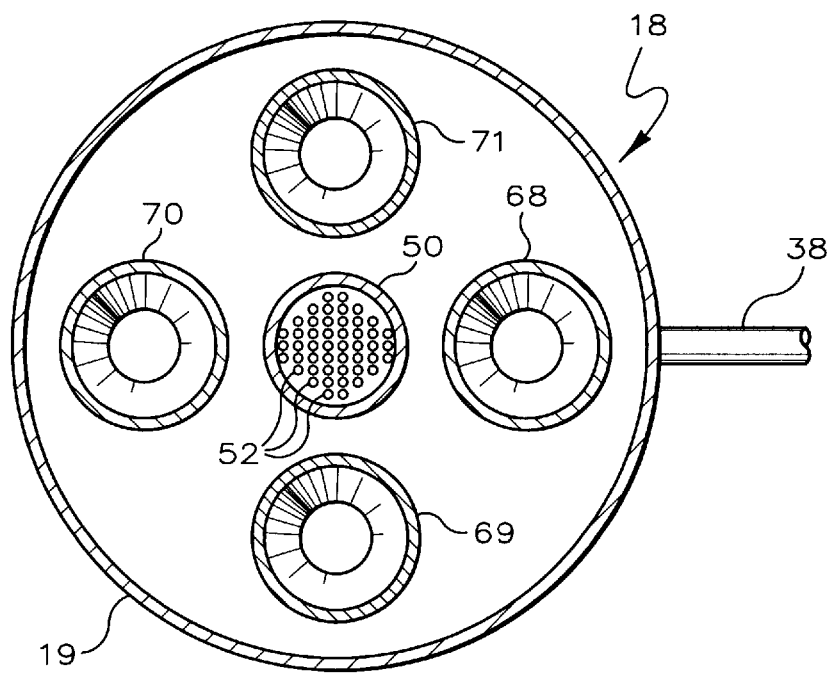
FIG. 5 is a sectional plane view, similar to that of FIG. 4, of an apparatus according to the invention utilizing four internal heat exchangers.

Referring now to FIG. 5, a sectional view, similar to that of FIG. 4, is illustrated. The alkylation reactor illustrated in FIG. 5 differs from that of FIG. 4 in that the embodiment illustrated utilizes four heat exchangers 68, 69, 70 and 71.

Figure 6:
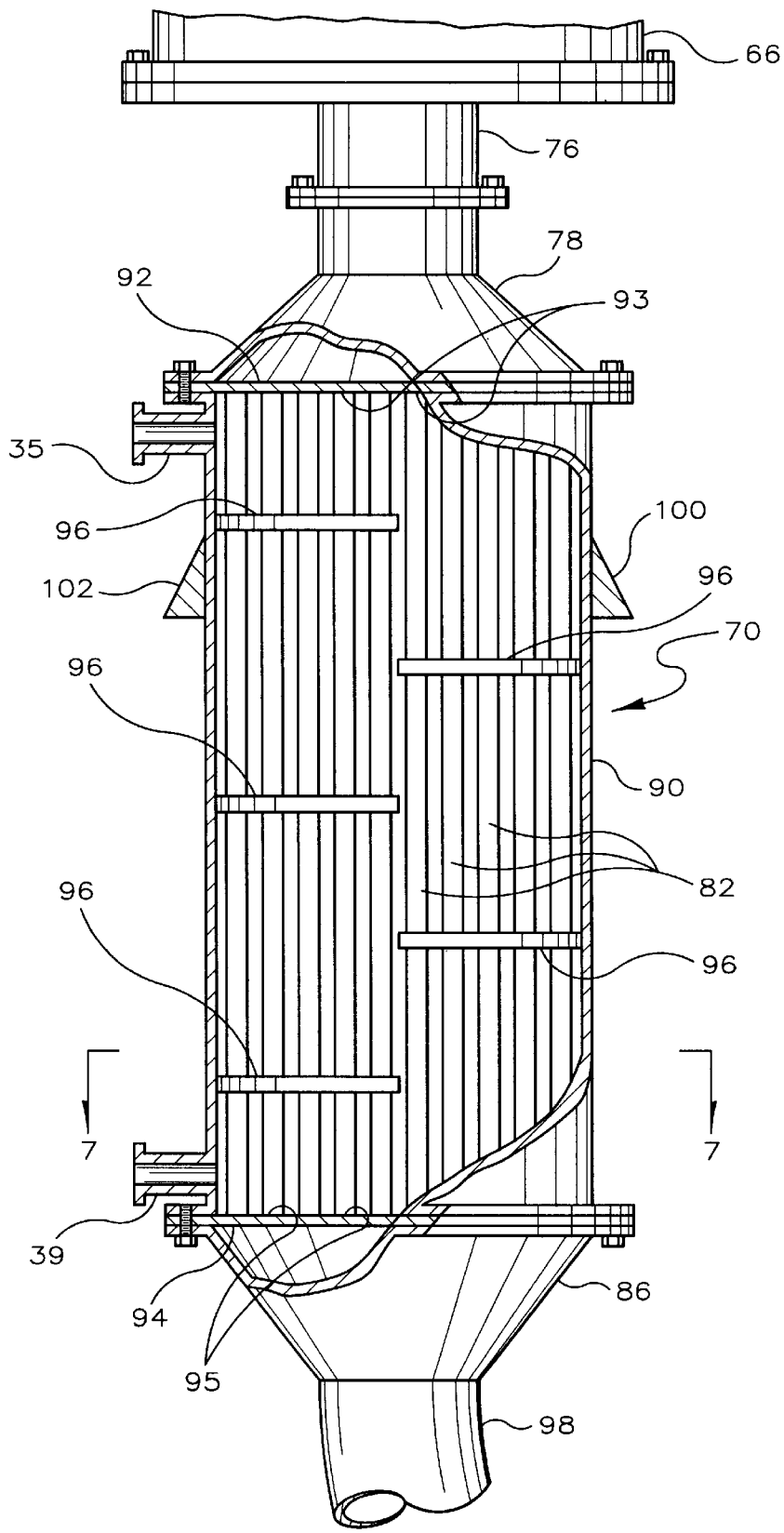
FIG. 6 is an elevated view, with portions of the shell broken away to more clearly illustrate the internal structure, showing a heat exchanger suitable for use in an apparatus according to the present invention.
Figure 7:
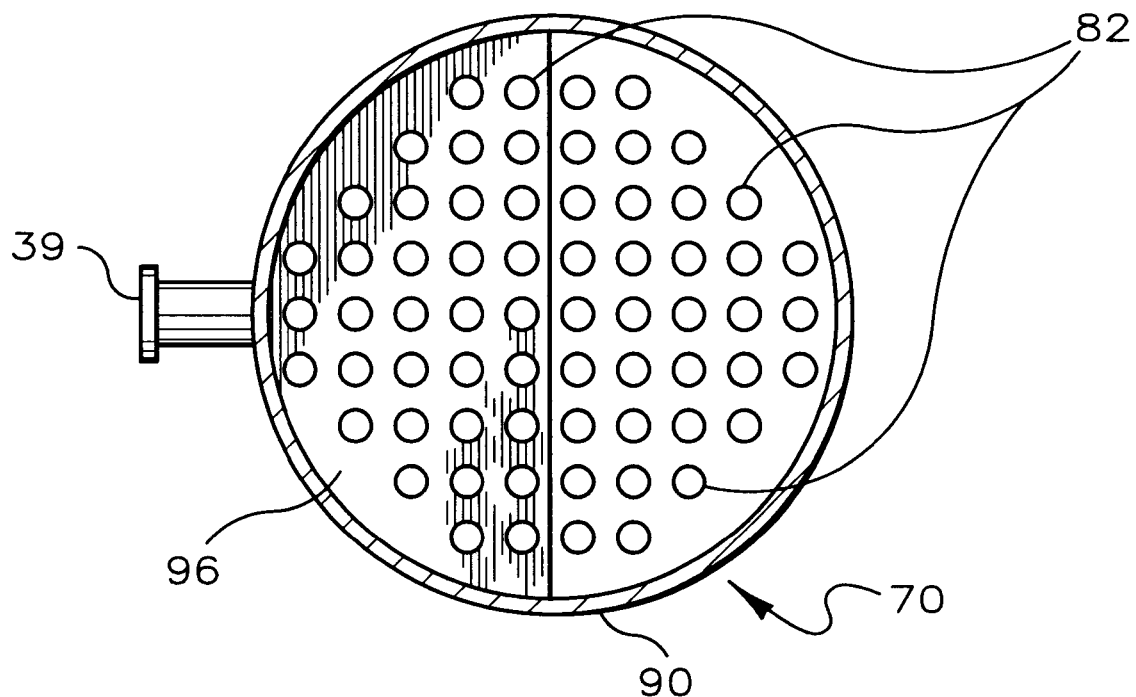
FIG. 7 is a sectional plane view through a portion of the lower end of the heat exchanger of FIG. 6, taken along line 7—7 of FIG. 6 of the drawing.

Referring now to FIGS. 6 and 7, a heat exchanger suitable for use in the current invention is illustrated. Heat exchanger 70 is a shell-and-tube heat exchanger having shell 90 and tube plates 92 and 94. A plurality of vertically disposed tubes 82 extend from tube plate 92 to tube plate 94. Tubes 82 form a plurality of parallel rows of tubes each tube having an upper tube end 93 and a lower tube end 95. Baffle plates 96 are provided to support the tubes and to direct flow through the shell side of the heat exchanger.

In operation, acid catalyst from nozzle 66 enters spool 76 and flows into heat exchanger endcap 78. From there, acid catalyst is distributed among and flows through tubes 82. The acid catalyst enters tubes 82 through upper tube end 93. During the passage through tubes 82, the acid catalyst is cooled by indirect heat exchange with the shell side coolant. The tubes are in fluid flow communication with endcap 86 and conduit 98. Thus, the acid catalyst flows out of tubes 82 through lower tube end 95 and into heat exchanger endcap 86 and from there flows into conduit 98 which is in fluid flow communication with chamber 58 of FIG. 2. The shell side coolant enters the shell side of the heat exchanger through conduit 39 and flows upwards through the heat exchanger. The flow of the shell side fluid is directed by baffle plates 96. The shell side fluid exits the shell side of the heat exchanger through conduit 35 and is cooled and recycled back to conduit 39 for further heat exchange.

Heat exchanger 70 has support brackets 100 and 102, which may be used to aid in supporting the heat exchanger within the alkylate reactor. The support of the heat exchanger can better be seen in FIG. 2 where support brackets 100 and 102 are seen supporting the heat exchanger by resting upon their mates, brackets 104 and 106. Brackets 104 and 106 are attached to the alkylation reaction vessel shell 19 and the riser-reactor conduit, respectively. Similarly, heat exchanger 68 has brackets 108 and 100 which rest upon their mates 112 and 114, respectively.

Returning now to FIG. 6, spool 76 can be disengaged from nozzle 66 and heat exchanger endcap 78 so that heat exchanger 70 can be removed from alkylate reactor vessel 18 through nozzle 66 and the top of the reactor vessel 18. Thus, the heat exchanger can be removed from the reactor vessel for maintenance purposes. However, it is within the scope of this invention for other methods to be used to remove the heat exchanger for maintenance purposes. Alternative methods include providing a flange opening in the bottom of alkylation reactor vessel 18 and removing the heat exchanger through the bottom of the reactor vessel or providing a flanged access panel on the side of the reactor vessel and sliding the exchangers out through the access panel opening.

As described above and illustrated in the Figures, the inventive alkylation reactor reduces the necessary acid inventory in the overall alkylation process by placing the coolers directly beneath the settler and thus eliminating the need for horizontal conduits between the reactor, the settling vessel and the acid coolers. Additionally, the present invention provides for further reduction in the amount of acid inventory by reducing the vertical conduits necessary between the settler, the heat exchangers and the riser-reactor conduit. Finally, by confining the riser-reactor conduit, settler and acid catalyst heat exchangers in one vessel, preferably a double-walled vessel, the present invention provides for a reduction in the possibility of the acid catalyst leaking into the atmosphere.

The following control and Example are given to illustrate acid inventory volume requirements of an alkylation process utilizing external acid cooling zones as compared to an alkylation process utilizing a reactor having internal cooling zones. The reactors described were not actually constructed, nor were the alkylation processes actually carried out, rather, the acid catalyst volume requirements of each alkylation process were calculated from the conditions associated with each reactor design as well as the design of any settlers or coolers.

CONTROL

The HF inventory is calculated for an alkylation reaction process utilizing two reactors, a settler and four coolers. The hydrocarbons to be reacted and the HF catalyst are introduced into the two reactors. Each reactor comprises a conduit having a 48-inch diameter. Effluent from the reactor is introduced into the settler, having a 20.5 ft. diameter, where HF catalyst is separated out and sent via conduits to the four coolers. Each cooler has 1,896 tubes of 1-inch diameter. After the catalyst is cooled in the coolers, it is returned to the reactor via conduits. The total hydrocarbon (HC) flow through the reactors, the HF catalyst flow through the reactors and the total acid inventory required are given in Table 1.

EXAMPLE

The HF inventory is calculated for an alkylation reaction process, according to the invention, utilizing a reactor vessel having a central reactor conduit, a settler located above the reactor conduit, and four coolers. The hydrocarbons to be reacted are introduced into the reactor conduit, mix with HF catalyst and carry HF catalyst up and through the reactor conduit. The conduit has a 54-inch diameter. Effluent from the reactor enters the settler, having a 20.5 ft. diameter, where HF catalyst is separated out of the effluent and flows generally downward into the coolers. Each cooler has 1,857 tubes of 1-inch diameter. After the catalyst is cooled, it enters the bottom portion of the vessel where it is again mixed with hydrocarbons entering the reactor conduit. The total hydrocarbon (HC) flow through the reactor conduit, the HF catalyst flow through the reactor and the total acid inventory required are given in Table 1.

TABLE 1

|  | Control | Example |
| --- | --- | --- |
| Reactor HC Flow | 1,191,907 lb/hr | 1,191,907 lb/hr |
| Reactor HF Flow | 8,148,549 lb/hr | 8,148,549 lb/hr |
| Total Acid Inventory | 454,417 lb | 147,107.5 lb |

It can be seen from the Example that the method and apparatus described above provides advantages over prior alkylation methods and apparatus, including a reduction in the acid inventory requirements.

Reasonable variations and modifications which will be apparent to those skilled in the art can be made in this invention without parting from the spirit and scope thereof.

What is claimed is:

1. An apparatus for contacting a feed with an acid catalyst to produce a product which comprises:

a vertically disposed vessel having an upper end portion and a lower end portion;

an acid settler contained within said vessel and located in said upper end portion;

a riser-reactor conduit vertically disposed within said vessel and having an inlet in fluid flow communication with said lower end portion and an outlet in fluid flow communication with said acid settler;

first means for introducing said feed into said housing at said lower end portion such that said feed moves upward through said riser-reactor conduit carrying with it acid catalyst contained in said lower end portion; and a heat exchanger vertically disposed within said vessel, wherein said heat exchanger is detachably engaged within said vertically disposed vessel such that said heat exchanger can be disengaged and removed from said vertically disposed vessel, said exchanger comprising a shell having a heat exchange fluid inlet and a heat exchange fluid outlet, a plurality of vertically disposed tubes forming a plurality of parallel rows of tubes, each tube having an upper tube end and a lower tube end, an acid inlet in fluid flow communication with said acid settler and said upper tube end of each tube, and an acid outlet in fluid flow communication with said lower tube end of each tube and said lower end portion of said vessel, said exchanger being located beneath said acid settler and extending between said upper end portion and said lower end portion such that acid catalyst from said settler flows into said acid inlet and through said tubes and subsequently flows out said acid outlet and into said lower end portion of said vessel.

2. An apparatus according to claim 1 wherein said riser-reactor conduit is positioned substantially along the central vertical axis of said vessel and said shell-and-tube heat exchanger is positioned substantially parallel to and spaced from the riser-reactor conduit.

3. An apparatus according to claim 1 wherein said first means for introducing feed comprises a spray nozzle that injects feed up and into the riser-reactor conduit.

4. An apparatus according to claim 1 further comprising a second means for introducing feed wherein said second means for introducing feed introduces said feed above said first means for introducing feed and inside said riser-reactor conduit.

5. An apparatus for contacting a hydrocarbon mixture comprising an olefinic hydrocarbon and an isoparaffin with an acid catalyst to form an alkylate product comprising:

a vertically disposed vessel having an upper end portion and a lower end portion;

an acid settler contained within said vessel and located in said upper end portion wherein in said acid settler said acid catalyst is separated from said alkylate such that said acid catalyst flows generally toward the bottom of the acid settler due to it having a greater density than said alkylate;

a riser-reactor conduit vertically disposed within said vessel and having an inlet in fluid flow communication with said lower end portion of said vessel and at outlet in fluid flow communication with said acid settler;

first means for introducing said hydrocarbon mixture wherein said first means introduces said hydrocarbon mixture into said vessel at said lower end portion such that said hydrocarbon mixture moves upward through said riser-reactor conduit carrying with it acid catalyst contained in said lower end portion;

second means for introducing said hydrocarbon mixture wherein said second means introduces said hydrocarbon mixture into said riser-reactor above said first means such that said hydrocarbon mixture moves upward through said riser-reactor conduit;

a heat exchanger vertically disposed within said vessel, wherein said heat exchanger is detachably engaged within said vertically disposed vessel such that said heat exchanger can be disengaged and removed from said vertically disposed vessel, said exchanger comprising a shell having a heat exchange fluid inlet and heat exchange fluid outlet, a plurality of vertically disposed tubes forming a plurality of parallel rows of tubes, each tube having an upper tube end and a lower tube end, an acid inlet in fluid flow communication with said acid settler and said upper tube end of each tube, and an acid outlet in fluid flow communication with said lower tube end of each tube and said lower end portion of said vessel, said exchanger being located beneath said acid settler and extending between said upper end portion and said lower end portion such that acid catalyst from said settler flows into said acid inlet and through said tubes and subsequently flows out said acid outlet and into said lower end portion of said vessel.

6. An alkylation process which comprises:

a) introducing a plurality of streams of a hydrocarbon mixture of isoparaffin and olefinic hydrocarbons into the lower portion of a vertically disposed vessel containing a separated steam of liquid acid catalyst so that said hydrocarbon mixture and said acid catalyst commingle and travel generally upward through a vertically disposed central riser-reactor conduit contained within said vessel;

b) introducing an additional plurality of streams of said hydrocarbon mixture within said riser-reactor conduit and above said lower portion of said vessel;

c) reacting said olefin and isoparaffin in the presence of said acid catalyst within said riser-reactor conduit to form reacted hydrocarbons;

d) subsequently, passing said acid catalyst and said reacted hydrocarbons into an acid settling zone contained within the upper portion of said vessel wherein said acid catalyst separates from said reacted hydrocarbons by means of said reacted hydrocarbons having a lesser density than said acid catalyst such that said less dense reacted hydrocarbons flow generally upward and said more dense acid catalyst flows generally downward;

e) subsequently, passing said acid catalyst into at least one cooling zone contained within said vessel and located beneath said acid settling zone and above said lower portion of said vertically disposed vessel, said cooling zone comprising a heat exchanger vertically disposed with said vessel, wherein said heat exchanger is detachably engaged within said vertically disposed vessel such that said heat exchanger can be disengaged and removed from said vertically disposed vessel, said exchanger comprising a shell having a heat exchange fluid inlet and a heat exchange fluid outlet, a plurality of vertically disposed tubes forming a plurality of parallel rows of tubes, each tube having an upper tube end and a lower tube end, and acid inlet in fluid flow communication with said acid settler and said upper tube end of each tube, and an acid outlet in fluid flow communication with said lower tube end of each tube and said lower end portion of said vessel, wherein as said acid catalyst continues to flow downward it is cooled by indirect heat exchange with a coolant to form a cooled acid catalyst; and f) passing said cooled acid catalyst into the lower portion of said vessel as the separated stream of liquid acid catalyst.

\* \* \* \* \*